United States Patent [19]

Quack et al.

[11] Patent Number: 4,654,163
[45] Date of Patent: Mar. 31, 1987

[54] NONIONIC FLUENT PEARL LUSTER DISPERSIONS

[75] Inventors: Jochen M. Quack, Eppstein; Alwin Reng, Kelkheim; Werner Skrypzak, Liederbach; Walter Kunz, Hattersheim am Main, all of Fed. Rep. of Germany

[73] Assignee: Hoechst Aktiengesellschaft, Fed. Rep. of Germany

[21] Appl. No.: 716,047

[22] Filed: Mar. 26, 1985

[30] Foreign Application Priority Data

Mar. 28, 1984 [DE] Fed. Rep. of Germany ....... 3411328

[51] Int. Cl.$^4$ .......................... A61K 7/06; B01J 13/00
[52] U.S. Cl. ........................... 252/312; 252/DIG. 13; 252/544; 252/548; 424/70
[58] Field of Search ......... 424/70; 252/548, DIG. 13, 252/312

[56] References Cited

U.S. PATENT DOCUMENTS

| | | | |
|---|---|---|---|
| 4,102,795 | 7/1978 | Minegishi et al. | 424/70 |
| 4,126,674 | 11/1978 | Mausner | 424/70 |
| 4,384,974 | 5/1983 | Guthauser | 424/170 |
| 4,438,096 | 3/1984 | Preston | 424/70 |
| 4,486,334 | 12/1984 | Horiuchi et al. | 252/312 |
| 4,503,033 | 3/1985 | Bouillon et al. | 549/445 |

FOREIGN PATENT DOCUMENTS

| 56-71021 | 6/1981 | Japan | 424/70 |
|---|---|---|---|
| 2121072 | 12/1983 | United Kingdom | 252/312 |

*Primary Examiner*—Dale R. Ore
*Attorney, Agent, or Firm*—Connolly and Hutz

[57] ABSTRACT

Pearl luster dispersions comprising a fatty acid glycol ester, a fatty acid alkanolamide, a nonionic surfactant of the formula $$R_5-O-(A-O)_m-(B-O)_n-R_6$$

where $R_5$ denotes $C_8$–$C_{30}$-alkyl or alkenyl, $R_6$ denotes hydrogen or a group of the formula —$CH_2O$—$R_7$, $R_7$ denotes $C_1$–$C_{10}$-alkyl or alkenyl, A and B, independently of each other, denote a group of the formula —$C_2H_4$— or —$C_3H_6$—, and m and n each denote a number from 1 to 30, and water to 100%.

Pearl luster dispersions based on this nonionic surfactant have the advantage that they are fluent even at temperatures below 20° C.

6 Claims, No Drawings

NONIONIC FLUENT PEARL LUSTER DISPERSIONS

To improve the visual aspect of cosmetic hair-cleaning and body-cleaning agents, washing-up liquids and liquid detergents and cleaners, use is frequently made of sub-stances which confer on said products a look like pearl luster. Such a pearly or silky luster effect can be obtained with various known substances, for example pulverulent natural materials, such as mica or pearl essence (modified fish scales), inorganic materials, such as bismuth oxichloride and titania pigments, and metal salts of higher fatty acids, fatty acid glycol esters and fatty acid alkanolamides mixed with other surfactants.

A technique which has been widely used in recent years involves using a fatty acid glycol ester alone or in combination with fatty acid alkylolamides. Since said materials are solid non-crystalline substances, it is necessary in the preparation of cosmetic washing and cleaning agents having a pearl luster effect to heat the batch to above the melting point of the pearlescent substances used. In this case the result after the heating is a homogeneous melt which, on cooling down and producing crystals, results in a pearl luster effect. However, this technique has the disadvantage that the entire production batch used therein needs to be raised to a suitable temperature (about 60°-80° C., depending on the pearlescent substance) and precisely defined cooling and stirring conditions are necessary before a more or less uniform constant pearl luster is obtained. All that consumes a comparatively large amount of energy and time.

The addition of substances which are sensitive to heat or warmth, such as ethereal oils, perfume oils and certain active substances, cannot take place before the cooling process has ended. Nor is it possible to adapt this technique for the continuous preparation of cosmetic products having a pearl luster effect.

Because of the disadvantages described above, a trend has taken hold in recent years towards room temperature methods of preparing cosmetic hair-cleaning and body-cleaning agents having a pearl luster effect. In these methods, so-called pearl luster dispersions, based on various pearlescent substances, are used in combination with surfactants, the pearl luster effect being obtained by incorporating the pearlescent substance in high concentration and at above the melting point into the surfactant which is likewise present in high concentration. The precise cooling and stirring conditions under which the incorporation is carried out bring about the formation of pearl luster crystals having a defined particle size distribution.

The substances which are used at present for preparing these pearl luster dispersions are fatty acid monoglycol and/or polyglycol esters which are incorporated alone or combined with alkanolamides in anionic surfactants, such as, for example, alkyl sulfates or polyoxyalkylene alkyl sulfates (alkyl ether sulfates), as solvents or dispersants. The result is usually that the dispersions obtained are very viscous and no longer fluent at lower temperatures.

Owing to the high alkyl sulfate or alkyl ether sulfate content, these pearl luster dispersions have the following disadvantages:

incompatibility with cationic surfactants—in cationic formulations, such as hair conditioners and fabric softeners, the present pearl luster concentrates form neutral salts which are in some cases insoluble, thereby weakening the cationic charge and thus reducing the desired effect; sensitivity of the alkyl sulfates or alkyl ether sulfates to hydrolysis, especially at low pH (<pH 5); pronounced foaming in processing, owing to the presence of large amounts of surfactants having pronounced foaming properties; high viscosity at low temperatures and hence difficult handling in transport and processing; formulations free of alkyl sulfate or alkyl ether sulfate impossible; and presence of toxicologically unsafe dioxane on using pearl luster concentrates containing alkyl ether sulfate.

Extensive studies were carried out with the object of eliminating the abovementioned disadvantages of the pearl luster dispersions on the market. It was found, surprisingly, that the pearl luster dispersions obtained on using fatty acid monoglycol and/or polyglycol esters in combination with fatty acid alkanolamides, in addition to having an excellent pearl luster effect and a long shelf life, do not have the abovementioned disadvantages when the wetting agent or dispersant used is a non-ionic surfactant of the type defined hereinafter.

The invention accordingly provides nonionic fluent pearl luster dispersions comprising 5-30% by weight of a fatty acid glycol ester of the formula I

where $R_1$ denotes a linear or branched, saturated or unsaturated hydrocarbon chain of 13-21 carbon atoms, A denotes a group of the formula $-C_2H_4-$ or $-C_3H_6-$, preferably $-C_2H_4-$, x denotes a hydrogen atom or a group of the formula

and m denotes a number from 1 to 10, preferably 1 to 3, 2-20% by weight of a fatty acid alkanolamide of the formula II

where $R_2$ denotes a linear or branched, saturated or unsaturated hydrocarbon chain of 7-29 carbon atoms, and $R_3$ and $R_4$, independently of each other, denote a hydrogen atom or a group of the formula $-C_2H_4OH$ or $-C_3H_6OH$, 0.1-10% by weight of a non-ionic surfactant of the formula III $$R_5-O-(A-O)_m-(B-O)_n-R_6 \qquad (III)$$

where $R_5$ denotes a linear or branched, saturated or unsaturated hydrocarbon group of 8-30, preferably 10-18, carbon atoms, $R_6$ denotes a hydrogen atom or a group of the formula

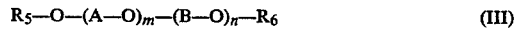

$R_7$ denotes a linear or branched, saturated or unsaturated hydrocarbon group of 1-10, preferably 3-5, carbon atoms, A and B, independently of each other, denote a group of the formula —$C_2H_4$ or —$C_3H_6$—, and n and m each denote an integer from 1 to 30, preferably 3 to 10, and water to 100%.

Using the four components within the abovementioned concentration level ranges and complying with the conditions described hereinafter produces optimal pearl luster dispersions which, compared with the pearl luster dispersions currently available on the market, have the following advantages:

(a) nonionic structure; hence no chemical reaction with cationic surfactants.

(b) remarkably favorable flow properties even at relatively low temperatures.

(c) very low surfactant content.

(d) free of alkyl sulfates or alkyl ether sulfates.

(e) substantial reduction of the dioxane content.

There now follows a description of the components required for preparing pearl luster dispersions of the invention having optimal application properties and of the concentrations in which the components are employed therein.

Suitable pearlescent substances are the fatty acid glycol esters of the formula (I) and mixtures of this class of substance. The most favorable properties are shown by compounds in which $R_1$ is an alkyl radical of 15-17 carbon atoms, m is 1 and x is a radical of the formula $R_1$—CO—. These components are preferably used in a concentration of 10-20% by weight, the optimal concentration having been found to be 16%.

Preferred fatty acid alkanolamides of the formula (II) have a distribution of 10-18 carbon atoms in the parent fatty acid. Of these, preference is given to fatty acid monoethanolamides in which one of the two radicals $R_3$ or $R_4$ in the formula (II) represents a hydrogen atom and the other radical represents a group of the formula —$C_2H_4OH$.

This component is preferably used in a concentration of 2-10%, in particular 4%.

It has been found that, of the suitable nonionic surfactants of the formula III, compounds in which $R_5$ represents an alkyl group of 10-18 carbon atoms, which may be linear or branched, and m and n each represent 4 are especially advantageous. This nonionic component is preferably used in a concentration of 0.5-5%, in particular 2%. The water used in the present invention is demineralized water.

The procedure for preparing the pearl luster dispersion according to the invention is as follows. A mixing vessel (heatable boiler) is charged with the two components of the formulae I and II, and the mixture is then heated to about 76° C., turning into a melt. This melt has added to it with stirring a hot aqueous solution of the component of the formula III likewise at 75° C. The speed of stirring should not be excessively high and should be about between 10 and 100 revolutions per minute. The resulting dispersion is stirred at a temperature of 75° C. for approximately a further 30 minutes. The dispersion is then cooled down with stirring to an end temperature of 20°-30° C. The rate of cooling should take place under controlled conditions, namely in the same way as is the practice with hitherto customary pearl luster dispersions to obtain a constant, reproducible pearl luster effect.

In the course of cooling, the two components I and II start to crystallize at about 50°-60° C. and form the desired pearl luster.

In addition to the abovementioned main components, the pearl luster dispersion according to the invention can also contain additives such as preservatives, buffer substances and electrolytes. The pH of the dispersion is within the range from 4 to 9, preferably from 5 to 8.

The present pearl luster dispersion according to the invention can be added to such hair-cleaning and body-cleaning agents, dishwashing agents, detergents and cleaners as are liquid at room temperature. The results are end products which exhibit a remarkable pearl luster. The amount of pearl luster dispersion needed to ensure the desired effect is generally between 1 and 10%.

Since the pearl luster dispersion according to the invention has a comparatively low viscosity at temperatures above 10° C., it is possible to process the dispersion by means of automatic pumping, metering and mixing machinery. That is of particular interest in the fully continuous production of finished products having a pearl luster effect.

Pearl luster dispersions according to the invention are described in the following examples. The indicated quantities are in each case percentages by weight. "EO" means ethylene oxide and "PO" propylene oxide.

EXAMPLE 1

| Composition | |
|---|---|
| Monoethylene glycol distearate | 16.0% |
| Cocomonoethanolamide | 4.0% |
| $C_{10/12}$—fatty alcohol + 4 EO + 4 PO | 2.0% |
| Water, preservative | to 100.0% |

EXAMPLE 2

| Composition | |
|---|---|
| Monoethylene glycol distearate | 10.0% |
| Cocomonoethanolamide | 10.0% |
| $C_{10/12}$—fatty alcohol + 4 EO + 4 PO | 2.0% |
| Water, preservative | to 100.0% |

EXAMPLE 3

| Composition | |
|---|---|
| Monoethylene glycol distearate | 16.0% |
| Cocomonoethanolamide | 4.0% |
| $C_{10/12}$—fatty alcohol + 4 EO + 4 PO | 2.0% |
| Water, preservative | to 100.0% |

EXAMPLE 4

| Composition | |
|---|---|
| Triethylene glycol distearate | 16.0% |
| Cocomonoethanolamide | 4.0% |
| $C_{10/12}$—fatty alcohol + 4 EO + 4 PO | 2.0% |
| Water, preservative | to 100.0% |

EXAMPLE 5

| Composition | |
|---|---|
| Triethylene glycol distearate | 10.0% |
| Cocomonoethanolamide | 10.0% |
| $C_{10/12}$—fatty alcohol + 4 EO + 4 PO | 2.0% |
| Water, preservative | to 100.0% |

These pearl luster dispersions specified in Examples 1-5 were tested from the following aspects:
1. assessment of the pearl luster effect
2. determination of the optical density
3. viscosity or flow behavior
4. shelf life at temperatures higher and lower than room temperature.

The test methods used were those customary in the cosmetic industry. The pearl luster effect was assessed visually in comparison to commercially available pearl luster dispersions. The optical density was determined photometrically on 0.5 g/l dilutions in water by means of a Dr. Lange turbidimeter.

Tested from these aspects the pearl luster dispersions described in Examples 1-5 have excellent properties which are comparable to those of commercially available products or, in some cases, are better than those of commercially available products. However, unlike these commercially available dispersions, the dispersions according to the invention are fluent even below 20° C.

We claim:

1. A non-ionic fluent pearl luster dispersion consisting essentially of 5-30% by weight of a fatty acid glycol ester of the formula I

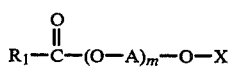
$$R_1-\overset{O}{\underset{\|}{C}}-(O-A)_m-O-X \qquad (I)$$

where $R_1$ denotes a saturated or unsaturated hydrocarbon chain of 13-21 carbon atoms, A denotes a group of the formula $-C_2H_4-$ or $-C_3H_6-$, preferably $-C_2H_4-$, X denotes a hydrogen atom or a group of the formula

$$R_1-\overset{O}{\underset{\|}{C}}-$$

and m denotes a number from 1 to 10, 2-20% by weight of a fatty acid alkanolamide of the formula II

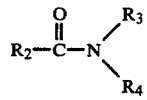
$$R_2-\overset{O}{\underset{\|}{C}}-N\overset{R_3}{\underset{R_4}{\diagdown}} \qquad (II)$$

where $R_2$ denotes a saturated or unsaturated hydrocarbon chain of 7-29 carbon atoms, and $R_3$ and $R_4$, independently of each other, denote a hydrogen atom or a group of the formula $-C_2H_4OH$ or $-C_3H_6OH$, 0.1-10% by weight of a non-ionic surfactant of the formula III

$$R_5-O-(A-O)_m-(B-O)_n-R_6 \qquad (III)$$

where $R_5$ denotes a saturated or unsaturated hydrocarbon group of 8-30 carbon atoms, $R_6$ denotes a hydrogen atom or a group of the formula

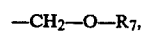
$$-CH_2-O-R_7,$$

$R_7$ denotes a saturated or unsaturated hydrocarbon group of 1-10 carbon atoms, A and B, independently of each other, denote a group of the formula $-C_2H_4-$ or $-C_3H_6-$, and n and m each denote a number from 1 to 30, and water to 100%.

2. A pearl luster dispersion as claimed in claim 1, wherein, in the formula I, $R_1$ denotes $C_{19}$-$C_{17}$-alkyl, X denotes a group of the formula $R_1CO-$ and m denotes 1, in the formula II $R_2$ denotes $C_9$-$C_{17}$-alkyl, $R_3$ denotes hydrogen and $R_4$ denotes a $C_2H_4OH$ group, and in the formula III $R_5$ denotes $C_{10}$-$C_{18}$-alkyl, $R_7$ denotes $C_3$-$C_5$-alkyl and m and n each denote 4.

3. A pearl luster dispersion as claimed in claim 1 which contains 10-20% by weight of the component of formula I, 2-10% by weight of the component of formula II and 0.5-5% by weight of the component of formula III.

4. A pearl luster dispersion as claimed in claim 1, wherein in formula I, m denotes a number from 1 to 3.

5. A pearl luster dispersion as claimed in claim 4, wherein in formula III, n and m each denote a number from 3 to 10.

6. A pearl luster dispersion as claimed in claim 1, wherein the formula III, n and m each denote a number from 3 to 10.

* * * * *